(12) United States Patent
Kahlman et al.

(10) Patent No.: US 8,990,059 B2
(45) Date of Patent: Mar. 24, 2015

(54) ANALYZING TOOL FOR AMPLIFICATION REACTIONS

(75) Inventors: Josephus Arnoldus Henricus Maria Kahlman, Eindhoven (NL); Tamara Mathea Elisabeth Nijsen, Eindhoven (NL); Bin Yin, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 340 days.

(21) Appl. No.: 13/500,431

(22) PCT Filed: Oct. 14, 2010

(86) PCT No.: PCT/IB2010/054646
§ 371 (c)(1),
(2), (4) Date: Apr. 5, 2012

(87) PCT Pub. No.: WO2011/048529
PCT Pub. Date: Apr. 28, 2011

(65) Prior Publication Data
US 2012/0197610 A1    Aug. 2, 2012

(30) Foreign Application Priority Data

Oct. 21, 2009    (EP) .................................... 09173608

(51) Int. Cl.
*G06G 7/48* (2006.01)
*G06F 19/24* (2011.01)

(52) U.S. Cl.
CPC ...................................... *G06F 19/24* (2013.01)
USPC ............................................................ 703/11

(58) Field of Classification Search
CPC ........ C40B 30/06; C40B 60/12; C40B 30/10; C40B 30/04; C12Q 1/68; C12P 19/34; G06F 19/00; G06F 19/18; G06F 19/22; G06F 19/12; G01N 21/64; G01N 21/76; G01N 33/48; B01L 7/00; C12N 15/00; C12N 15/11; C12N 9/12; C12N 9/96; C12M 1/26; C07H 21/04; C07C 229/12; C07C 227/18
USPC ......... 703/11, 12, 6; 435/6; 506/10; 205/792; 405/6
See application file for complete search history.

(56) References Cited

U.S. PATENT DOCUMENTS

| 6,783,934 | B1 | 8/2004 | McMillan et al. |
| 7,228,237 | B2 | 6/2007 | Woo et al. |
| 2006/0147955 | A1* | 7/2006 | Allawi et al. ..................... 435/6 |
| 2007/0111246 | A1* | 5/2007 | Carrick et al. .................... 435/6 |

(Continued)

FOREIGN PATENT DOCUMENTS

WO    WO2006048337    5/2006

OTHER PUBLICATIONS

W. Liu et al., "Validation of a Quantitative Method for Real Time PCT Kinetics", Biochemical and Biophysical Research Communications, Academic Press Inc., Orlando, FL, US, vol. 294, No. 2, Jun. 7, 2002, pp. 347-353.

(Continued)

*Primary Examiner* — Kandasamy Thangavelu

(57) ABSTRACT

The invention relates to a method and apparatus for obtaining information from an amplification curve of a target nucleic acid sequence or sequences by defining at least one model function that describes the amplification curve and that contains at least one parameter that is related to a physical quantity that influences the signals recorded, fitting said model function to the amplification curve, and obtaining information with respect to said physical quantity by identifying the value of said parameter that results in the best fit of the model function.

10 Claims, 7 Drawing Sheets

(56) References Cited

U.S. PATENT DOCUMENTS

| | | |
|---|---|---|
| 2009/0047679 A1* | 2/2009 | Shain et al. .................. 435/6 |
| 2009/0065372 A1* | 3/2009 | Marchal et al. ............... 205/792 |
| 2009/0068666 A1 | 3/2009 | Bartkowiak et al. |
| 2009/0082219 A1* | 3/2009 | Ermantraut et al. ........... 506/10 |
| 2009/0176232 A1* | 7/2009 | Ales et al. .................... 435/6 |
| 2010/0015630 A1* | 1/2010 | Gupta et al. .................. 435/6 |
| 2010/0041045 A1* | 2/2010 | Rueck et al. .................. 435/6 |
| 2010/0233686 A1* | 9/2010 | Higuchi et al. ................ 435/6 |
| 2011/0076674 A1* | 3/2011 | Blaschke-Bonkowsky et al. .................. 435/6 |

OTHER PUBLICATIONS

M.W. Pfaffl, "A new Mathematical Model for Relative Quantification in Real-Time RT-PCR", Nucleic Acids Research, Oxford University Press, Surrey, GB, vol. 29, No. 9, May 1, 2001, pp. E45.2002-E45.2007.

S.A.E. Marras, "Efficiencies of Fluorescence Resonance Energy Transfer and Contact-Mediated Quenching in Oligonucleotide Probes", Nucleic Acids Research, 2002, vol. 30 No. 21 e122, pp. 1-8.

J.D. Durtschi et al., Analytical Biochemistry, 361 (2007), pp. 55-64.

* cited by examiner

ANALYZING TOOL FOR AMPLIFICATION REACTIONS

FIELD OF THE INVENTION

The present invention is related to the field of nucleic acid quantification by means of the polymerase chain reaction (PCR).

BACKGROUND OF THE INVENTION

Quantification of nucleic acids is important in a number of fields ranging from molecular biology and genetic research to diagnostics and pathogen detection. When sufficient amounts of nucleic acids are present blot-techniques can be applied for quantification. However, the limited sensitivity of these techniques prevents their use in a number of cases.

Quantitative PCR methods developed in the recent past provided tools for analysis in cases where much higher sensitivity was required. These techniques are based on the fact that during PCR amplification the amount of product grows exponentially and, thus, the amount of product obtained after a small number of cycles can be detected by conventional means, (e.g., fluorescent detection). Further, in principle, the amount of product that was present initially, i.e., at the beginning of the amplification, can be determined from the amount of product obtained at the end of the amplification if the number of amplification cycles is known.

A typical plot of PCR product formed over the course of an amplification reaction reveals four different phases of the amplification process (see FIG. 1): (1) the ground phase (GP) where the fluorescent signal is dominated by background fluorescent and noise; (2) the exponential phase (EP) where the signal from the PCR product rises above ground level and increases exponentially; (3) the log-linear phase (LP) where the signal increases at a less than exponential rate due to decreasing amplification efficiency caused by such factors as the consumption of PCR reagents and the degradation of detection probes; (4) the plateau phase (PP) with marginal rise of the signal due to an increasing slowdown and eventual stop of the amplification reaction.

At present, however, no physical models are available that describe the development of the signals detected during the PCR process in a realistic fashion. Therefore, current methods for the quantification of nucleic acids require performing calibration steps involving performing the same PCR reactions to reference samples with known concentrations of standard and/or comparative nucleic acid sequences. Often times, the nucleic acid sequences used as standards are well known housekeeping genes. Briefly outlined, in practice, target nucleic acid sequences as well as standard and/or comparative samples are subjected to PCR under defined reaction conditions and formation of the PCR product, also called an amplicon, is monitored over the course of the amplification process. Detection of PCR product is achieved, for example, by means of fluorescently labeled hybridization probes or by means of deoxyribonucleic acid ("DNA")-intercalating fluorescent dyes that detect double stranded PCR product. The number of amplification cycles necessary to obtain a particular fluorescence threshold-level, designated as $C_t$-values, are determined, and the $C_t$-value of the target is compared to the $C_t$-values of the samples of a dilution series of a nucleic acid standard with known concentrations (absolute quantification). In order to determine the absolute quantity of the target a standard curve is constructed from the $C_t$-values of the standard samples and used to determine the initial concentration of the target. Alternatively, the $C_t$-value of the target is compared to the $C_t$-value of a single comparative nucleic acid of interest (relative quantification). In this case, the ratio of the $C_t$-values of target and comparative samples is determined and used to assess the ratio of the initial quantities of target and comparative nucleic acid sequences.

In general, the development of new methods for nucleic acid quantification is confronted with a number of challenges some of which stem from the fact that several applications require complete automation as will be discussed in more detail below and some of which are related to the calibration process.

The calibration process required by methods for nucleic acid quantification employing $C_t$-value determination introduces a number of potential limitations. First of all, the examination of standard samples requires additional experimental effort and resources. Secondly, these methods are based on the assumption that the amplification efficiency in standard and target samples is the same. Importantly, this assumption is not generally correct and, thus, provides a source of inaccuracy.

Additional challenges in the field of quantitative PCR are related to the growing need to analyze large numbers of samples in short intervals of time. As an ever increasing range of applications for quantitative PCR requires analysis of very large numbers of samples in a high-throughput fashion, e.g. in clinical practice, it is necessary to develop quantitative PCR methods that can be completely automated and require very little or no human interaction. This is of crucial importance in some cases as high throughput applications (e.g. in clinical practice) simply cannot be conducted in the required short periods of time if human interaction is required.

An additional benefit that could be realized with such automated methods would be an improved comparability of analytical data between different labs currently employing widely differing laboratory protocols for quantitative PCR. The issue is of paramount importance in view of an increasing number of labs using quantitative PCR techniques for basic research. Establishing an automated method as an objective reference for quantification experiments would drastically benefit these research efforts by enhancing consistency from lab to lab.

Two methods employing $C_t$-value determination are currently available for nucleic acid quantification that, in principle, appear suitable for complete automation: the second derivative maximum method and the sigmoidal curve-fitting method. For the second derivative maximum method the maximum of the second derivative of the amplification curve is determined numerically. The corresponding cycle is assumed to represent the end of the exponential growth phase, where the reaction begins to slow down to linear growth. This cycle number is used, analogously to $C_t$, for determining the quantity of the target. For the sigmoidal curve-fitting method a sigmoid function is modeled upon the amplification curve. The cycle number corresponding to the inflection point of the curve can be obtained from the model and is used, analogously to $C_t$, for determining the quantity of the target. The second derivative maximum method and the sigmoidal curve-fitting method, however, have been found to be of limited use for applications requiring high sensitivity (J D Durtschi et al., Analytical Biochemistry, 361 (2007), pp. 55-64). Furthermore, both of these methods require calibration steps. In addition the sigmoid function modeled upon the amplification curve in the process of employing the sigmoidal curve-fitting method is greatly idealized and can, by no means be regarded as a physical model describing the development of the signals detected during the PCR process.

SUMMARY OF THE INVENTION

It is, therefore, an object of the present invention to provide methods that are suitable for fully automated quantification of target nucleic acid sequences requiring high sensitivity. It is, further, an object of the present invention to provide methods that do not require comparison of target and standard samples, i.e., that require no calibration steps. In addition it is an object of the present invention to provide a physical model that allows the analysis of signals detected during the amplification process in great detail.

DETAILED DESCRIPTION OF THE EMBODIMENTS

Figure 1:
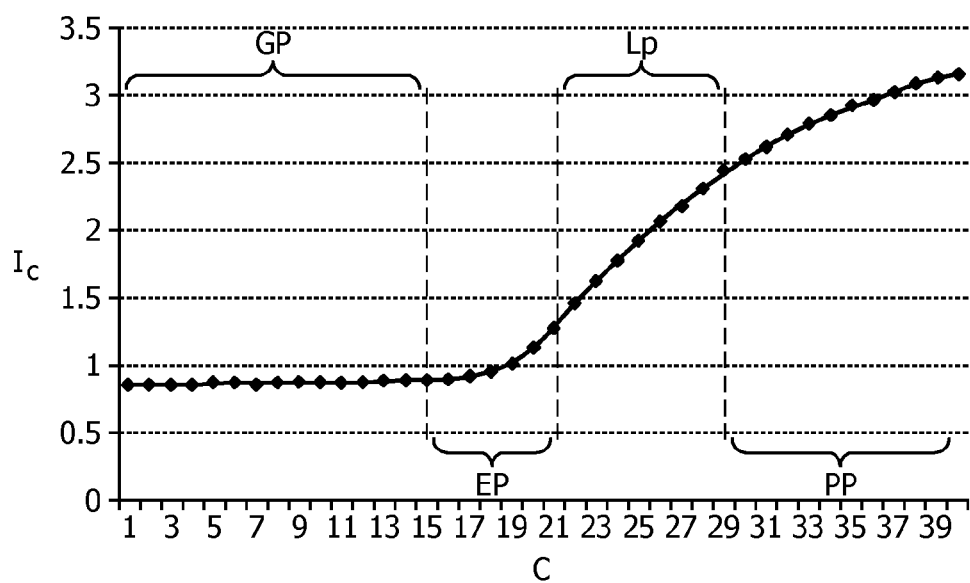
FIG. 1 shows a typical amplification curve obtained over the course of an amplification reaction revealing the different phases of the amplification process: GP=ground phase, EP=exponential phase, LP=log-linear phase, PP=plateau phase. C denotes the number of cycles and $I_C$ denotes the signal intensity recorded by the image analysis software employed by the experimenter. There are a number of these software programs well known by people of the art.

Nucleic acids that are amenable to the present invention comprise DNA, RNA as well as nucleic acids with modified backbone and/or base structures. Usually amplification is performed by the polymerase chain reaction (PCR) by methods and with the aid of instrumentation available to a person of skill in the art. However, for the purpose of this invention nucleic acids that cannot be amplified by PCR directly may have to be transcribed into DNA by means known to a person of skill in the art. RNA, for example, may have to be transcribed into DNA before amplification using a reverse transcriptase enzyme. In order to allow reconstruction of the original amounts of the corresponding nucleic acids such a transcription process has to be performed under conditions that enable reasonably well founded assumptions concerning the ratio of the amount of nucleic acid that was transcribed into DNA and the DNA that was produced in the course of transcription. Reaction conditions of this type are well known in the art.

Each nucleic acid sequence that is amplified in the course of practicing the present invention is usually amplified in a selective manner. One way to achieve selective amplification during PCR is the employment of specific sequence primers. Design and use of such primers are well known to persons of skill in the art.

For the purpose of the present invention, nucleic acid amplification by PCR, i.e., the production of nucleic acids, also known as amplicons, by the amplification reaction is detected by recording signals that are correlated to the amplification of said nucleic acid sequences. This is usually achieved by means of fluorescent reporter probes (also designated herein as fluorescent reporters or reporter probes). Such fluorescent reporter probes are well known in the art. In one embodiment of the present invention the fluorescent reporter probes comprise an oligonucleotide that specifically binds to the target nucleic acid sequence under hybridization conditions and carries a fluorescent group on one end of its sequence and a corresponding quencher group on the other end of its sequence. The close proximity of fluorescent group and quencher group in that state prevents emission of fluorescence. However, when the central oligonucleotide of the fluorescent reporter probe is broken down in the course of the next amplification cycle proximity of the fluorophore and the quencher is lost resulting in fluorescent emission. An increase in the amount of amplification product, i.e., the amplicon, therefore yields a proportional increase of fluorescence. In another embodiment of the present invention the fluorescent reporter probes are FRET (Fluorescence Energy Transfer) probes. In one embodiment of the present invention (Taq-Man) the fluorescent reporter probe is one of the PCR primers. In a preferred embodiment of the present invention nucleic acid amplification is detected with the aid of fluorescent reporter probes.

According to the present invention, signals correlated to the amplification of nucleic acid sequence are recorded over the course of an amplification reaction. Representation of the signals recorded over the course of the cycles of an amplification reaction is denoted as the amplification curve. Usually such signals are fluorescent emissions; however, other signals employed in the art are comprised in the present invention as well. Fluorescent emissions can be released by fluorescent dyes, several of which are known in the art. Some fluorescent dyes have absorption and emission spectra that are sufficiently separated to allow parallel detection in the same sample. The recording of signals over the course of an amplification reaction can be disturbed by optical crosstalk between the different color-channels in a chamber, which is a result of less than ideal optical filters and fluorophores. In addition auto-fluorescent of external components of the experimental setup can disturb the recording of signals, e.g., the plastic containers used for the reaction may respond to the excitation wavelengths and emit fluorescent. In a preferred embodiment of the present invention disturbances resulting from optical crosstalk and auto fluorescent are reduced by methods well known in the art. In a preferred embodiment of the present invention, representation of the signals recorded over the course of the cycles of an amplification reaction after reduction of disturbances resulting from optical crosstalk and auto fluorescent is denoted as the amplification curve. A simple way to reduce disturbances resulting from auto fluorescent is to determine a signal offset of the experimental setup in the presence of the container but in the absence of reagents used for the amplification reaction. The signals recorded during the amplification reactions are then corrected for this offset. A simple way to reduce disturbances resulting from optical crosstalk is to determine a crosstalk matrix describing crosstalk between different color channels by measuring known concentrations of unquenched fluorophores. This crosstalk matrix can be used to correct the signals recorded during the amplification reaction.

In the course of performing the methods of the present invention a model is defined that describes the amplification curve and that contains at least one parameter that is related to a physical quantity that has an impact on the signals recorded. The model can comprise one or several model functions. In a preferred embodiment the model comprises several model functions.

The physical quantity that has an impact on the signals recorded can be a quantity that is related to the amplification reaction itself or a quantity that is related to the measurement setup. In a preferred embodiment the physical quantity is related to the generation of signal noise during the amplification process. In another preferred embodiment the physical quantity is related to the inhibition of the amplification process. In another preferred embodiment the physical quantity is related to the spontaneous unquenching of fluorophores during the amplification process. In another preferred embodiment the physical quantity is selected from the following: (i) the absolute initial quantity of the target nucleic acid sequence, (ii) the initial amplification efficiency of the target nucleic acid sequence, (iii) the degree of inhibition of the amplification reaction, (iv) the degree of signal absorption by the reaction container used for the amplification process.

In the course of performing the methods of the present invention the model comprising at least one model function is fitted against the amplification curve. Methods for determining the best fit of such models are known in the art and chosen in accord with the model used. In a preferred embodiment the best fit of such a model is determined as follows: at first a cost-function is defined, e.g., a squared fitting error. This cost function can be weighted in order to emphasize particular parts of the curve, e.g., data points around $C_t$. Then an iterative Newton Raphson minimalisation, variable step-size method is used to minimize the cost function.

In the course of performing the methods of the present invention the parameter values are identified in the best fit of the model. The corresponding values contain information regarding the physical quantities that these parameters are related to.

In a preferred embodiment of the present invention, e.g., in the context of using TaqMan fluorescent reporter probes, the following model function IF(n) is defined that describes the amplification curve; the parameters related to physical quantities that have an impact on the signals recorded are chosen as the absolute initial quantity of the target nucleic acid sequence as $N_0$, and the parameters $E_0$, $\alpha$, $\epsilon$ and $\gamma$:

wherein $$IF[n] = \frac{N_{uq}[n]I_{uq} + N_q[n]I_q}{1+\gamma \cdot n},$$

and wherein $$N_q[n] = N_p - N_{uq}[n],$$

and wherein $$N_{uq}[n] = N[n] + N_{suq}[n],$$

and wherein $$N_{suq}[n] = N_{suq}[n-1] + \beta \cdot N_q[n-1],$$

and wherein $$N[n] = N[n-1](1+E[n]),$$

and wherein $$E[n] = E_0 - \alpha \left( \frac{N[n-1]}{N_p - N[n-1]} \right)^{\epsilon},$$

wherein:
n=cycle number;
N(n)=number of target nucleic acid molecules at cycle n;
$N_0$=N(0) absolute initial number of target nucleic acid sequence;
$N_{uq}$(n)=number of unquenched fluorescent reporters at cycle n;
$I_{uq}$=fluorescence intensity parameter for unquenched fluorescent reporters;
$N_q$(n)=number of quenched fluorescent reporters at cycle n;
$I_q$=fluorescent intensity parameter for quenched fluorescent reporters;
γ=parameter related to the absorption properties of the container used for performing the amplification process;
$N_p$=initial number of fluorescent reporter probes;
$N_{suq}$(n)=number of spontaneously unquenched fluorescent reporters at cycle n;
β=fraction of fluorescent reporters that unquench spontaneously;
E(n)=amplification efficiency of cycle n;
$E_0$=initial amplification efficiency;
α=scaling factor related to inhibition of the amplification process;
ϵ=parameter related to the sensitivity of the amplification process to PCR primer depletion.

Figure 2:
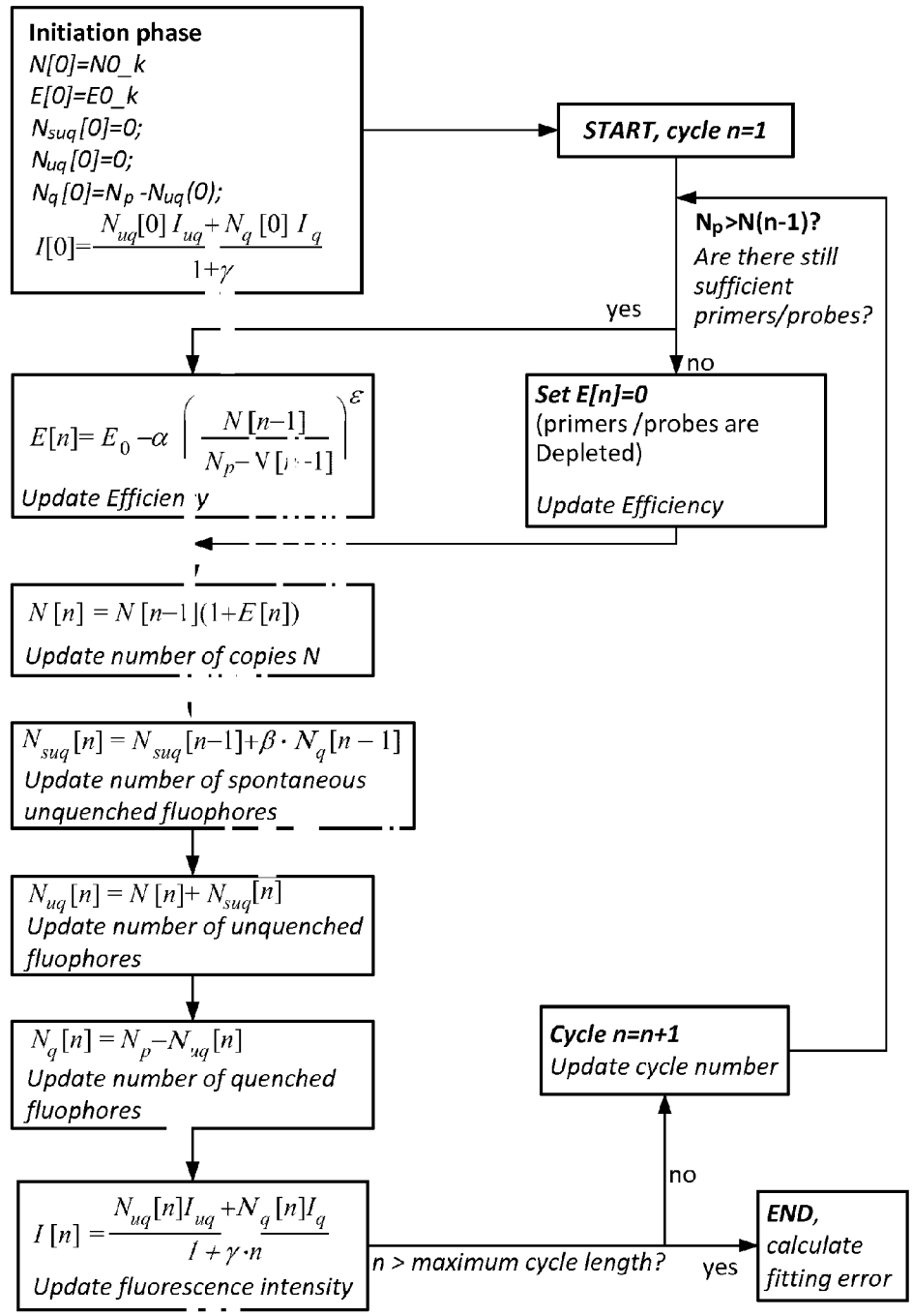
FIG. 2 shows a schematic representation of a method for determining a fit of model function IF(n) for the amplification curve.

In order to determine the best fit of the model to the amplification curve, the following operations are performed, as depicted in FIG. 2.

In a preparation phase a parameter space is defined for each of the parameters: $N_0$, α, $E_0$, ϵ, γ and divided into steps k1 to k5, i.e., [$N_0\_1$, $N_0\_2$, ..., $N_0\_k1$] for $N_0$, [α_1, α_2, ..., α_k2] for α, [$E_0\_1$, $E_0\_2$, ..., $E_0\_k3$] for $E_0$, [ϵ_1, ϵ_2, ..., ϵ_k4] for ϵ, [γ_1, γ_2, ..., γ_k5] for γ. The number of steps, k1 to k5, for the different parameters does not have to be the same, but can be suitably chosen in order to balance accuracy and computational effort. The parameter space covered by each parameter is defined in accordance with expected variations.

Furthermore, values for $I_q$, $I_{uq}$ and β are estimated as follows: in order to obtain an estimate for $I_q$ the signal intensity values for the first few cycles (e.g., from the first 1, 2, 3, 4, 5, 6, 7, 8, 9 or 10 cycles) of the amplification curve are averaged and divided by the initial number of fluorescent reporter probes $N_p$ yielding an estimate for $I_q$. An estimate for $I_{uq}$ is then determined according to $I_{uq}=I_q/(1-\eta_{QE})$ using $I_q$ as estimated before and the quenching efficiency $\eta_{QE}$ as described in the literature (e.g., S A E Marras et al. *Nucleic Acids Research* 2002, Vol. 30, Nr. 21, e122). The positive slope at the beginning of the amplification curve indicates a spontaneous unquenching of fluorophores; therefore the positive slope of the amplification curve during a series of early cycles (e.g., cycles 1 to 3, 1 to 5, 1 to 10, 3 to 10, or 5 to 10) can be used as an estimate for β. Further, a maximum cycle number $n_{max}$ is defined as the upper limit of the fitting interval, i.e., the amplification curve is fitted with IF(n) between cycles 0 and $n_{max}$. $n_{max}$ can, for example, be defined as the last cycle of the amplification process or, alternatively, as a cycle with a fixed number, e.g., as $n_{max}$=21, 22, 23, 24, 25, 26, 27, 28, 29, 30, 31, 32, 33, 34 or 35. Alternatively, $n_{max}$ can be defined as the cycle that follows a fixed number of cycles (e.g., 1, 2, 3, 4, 5, 6, 7, 8, 9, 10, 11, 12, 13, 14 or 15) after the $C_t$-value of the specific amplification curve, whereby the $C_t$-value can be determined by any method described in the art. Alternatively, $n_{max}$ can be defined as the last cycle where the amplification curve remains below a defined fraction of its maximum. In a preferred embodiment of the present invention $n_{max}$ is defined as the last cycle where the amplification curve remains below X % of its maximum, wherein X is selected from the group of 50, 55, 60, 65, 70, 75, 80, 85, 90, or 95. In another preferred embodiment of the present invention $n_{max}$ is defined as the cycle that follows 10 cycles after the $C_t$-value as determined by the second derivative maximum method.

In an initiation phase start-values are defined for a number of parameters. Cycle number n is set to n=0. Parameters $N_0$, α, $E_0$, ε, γ are assigned values from their corresponding parameter space. $N_p$ is defined as the initial number of fluorescent reporter probes that was used for the amplification process. $I_q$, $I_{uq}$ and β are defined according to the estimate performed before. $N_{suq}(0)$ is set to $N_{suq}(0)$=0. $N_{uq}(0)$ is set to $N_{uq}(0)$=0. $N_q(0)$ is set to $N_q(0)$=$N_p$−$N_{uq}(0)$. $I_0$ is set to $$I[0] = \frac{N_{uq}[0]I_{uq} + N_q[0]I_q}{1+\gamma}.$$

Subsequently the cycle number is set to n=1 and the following iterative process is performed:

Determine efficiency E(n) ("Step (a)")

$$E[n] = E_0 - \alpha\left(\frac{N[n-1]}{N_p - N[n-1]}\right)^\varepsilon,$$

Determine number of target nucleic acid sequences N(n) ("Step (b)")

$$N[n]=N[n-1](1+E[n]),$$

Determine number of spontaneously unquenched fluorescent reporters, $N_{suq}(n)$:

$$N_{suq}[n]=N_{suq}[n-1]+\beta \cdot N_q[n-1],$$

Determine number of unquenched fluorescent reporters $N_{uq}(n)$:

$$N_{uq}[n]=N[n]+N_{suq}[n],$$

Determine number of quenched fluorescent reporters $N_q(n)$:

$$N_q[n]=N_p-N_{uq}[n],$$

Determine fluorescent intensity I(n):

$$I[n] = \frac{N_{uq}[n]I_{uq} + N_q[n]I_q}{1+\gamma \cdot n}.$$

Evaluate n>$n_{max}$; YES=>calculate fitting error and proceed with the next set of parameter values for $N_0$, α, $E_0$, ε, γ; NO=>set n=n+1.

Evaluate $N_p$>N(n−1); YES=>proceed with step (a); NO=>set E(n)=0 and proceed with step (b).

The fitting error fit_err is calculated as a measure of the difference between the fit-function IF(n) and the amplification curve. The fit_err can be calculated by any method known in the art. For example, the fitting error fit_err can be calculated as:

$$\text{fit\_err}(N_0\_k1, \alpha\_k2, E_0\_k3, \varepsilon\_k4, \gamma\_k5) = \sum_{n=1}^{n_{max}}\left\{\frac{IF[n]-AC[n]}{AC[n]}\right\},$$

wherein AC(n) is the signal intensity value of the amplification curve at cycle n.

This process is repeated with different sets of values for parameters $N_0$, α, $E_0$, ε, γ until the parameter space has been covered sufficiently. Any method to select parameter values in order to efficiently obtain sufficient coverage of the parameter space known in the art can be applied. In a preferred embodiment all combinations of parameter values defined during the initiation phase are calculated.

The function IF(n) that yields the minimal fitting error for a specific amplification curve is then selected as the best fit and the corresponding parameter values $N_0^{\#}$, $\alpha^{\#}$, $E_0^{\#}$, $\varepsilon^{\#}$, $\gamma^{\#}$ are identified.

$N_0^{\#}$ represents the absolute initial number of target nucleic acid sequences that was determined. $N_0^{\#}$ represents the actual number of molecules that were present in the sample before the analysis it can be expressed as a fraction of the Avogadro Number in order to obtain an expression for the amount of substance.

The parameter, $\alpha^{\#}$, provides information about the inhibition of the amplification process.

The parameter, $E_0^{\#}$, yields information with respect to the efficiency of the amplification reaction, i.e., a PCR with poor efficiency can readily be identified from a low value of $E_0^{\#}$.

The parameter, $\varepsilon^{\#}$, is related to the sensitivity of the amplification process to PCR primer depletion.

The parameter, $\gamma^{\#}$, yields information with respect to the absorption properties of the container used for performing the amplification process.

In another embodiment the methods of the present invention can be used to obtain $C_t$-values in a fully automated fashion and with great accuracy and robustness. Methods according to this embodiment are useful in cases where external restraints dictate that a $C_t$-value has to be returned as a result instead of the absolute initial number of target nucleic acid sequences and/or other parameters. In order to obtain a $C_t$-value according to this embodiment an additional step (d) is performed, by using the best fit of said model function to determine a $C_t$-value for said amplification curve.

The best fit of the model function can be used by any method known in the art to determine a $C_t$-value for the amplification curve. In a preferred embodiment of the present invention the $C_t$-value is obtained from the best fit of the model function by employing the second derivative maximum method. Therefore, in a preferred embodiment of the present invention the second derivative maximum of the best fit is determined and used as a $C_t$-value.

In the context of the present invention cycle numbers that are obtained or defined (e.g. $C_t$-values) can be understood as integer cycle numbers or fractional cycle numbers. Depending on the particular context it is apparent to persons skilled in the art which types of cycle numbers should be employed. In a preferred embodiment of the present invention cycle numbers are to be understood as integer cycle numbers.

The present invention comprises methods and means for analyzing nucleic acid sequences. A single analysis can be directed at a single species of target nucleic acid sequence in a sample or more than one species of target nucleic acid sequence in a sample. In cases where more than one target nucleic acid sequence in a sample is subject to an analysis of the signals recorded to monitor the amplification of each target nucleic acid sequence have to be distinguishable signals, i.e., signals that can be recorded at the same time separately. Methods and means to achieve such signals are well known in the art. Some fluorescent dyes for example, exhibiting absorption and emission spectra that are sufficiently separated, allow parallel recording of their fluorescent signals at the same time. The present invention, thus, comprises multiplex analyses of several target sequences in a sample at the same time.

The present invention comprises methods and means to perform the methods of the invention in an automated fashion, i.e., without or with minimal human interaction. In a preferred embodiment the present invention is directed to methods and means to perform the methods of the invention without human interaction. The present invention enables a person of skill in the art to use instrumentation available in the art to perform the methods of the invention without or with minimal human interaction. In a preferred embodiment the present invention enables a person of skill in the art to use instrumentation available in the art to perform the methods of the invention without human interaction.

The present invention comprises machine readable media having stored thereon instructions for carrying out the methods of the invention.

The present invention further comprises an apparatus for the analysis of nucleic acid samples comprising a machine readable memory means containing information for carrying out the methods of the invention.

The present invention, further, relates to methods for the relative quantification of nucleic acid sequences. Relative quantification of nucleic acid sequences according to the present invention refers to obtaining a quantitative measure of the ratio of the amounts of the corresponding target nucleic acid sequences in a sample before the PCR reaction has begun.

According to the present invention comparative nucleic acid standards can be used to determine reference values for the relative quantification of the target nucleic acid sequences. One or several such comparative nucleic acid sequences in a sample can be used according to the present invention. The absolute quantity of a comparative nucleic acid sequence in a sample before the PCR reaction begins does not have to be known. Messenger RNAs, ("mRNAs"), of housekeeping genes in a cell, for example, can be used as comparative nucleic acid standards. In order to be amplified by PCR mRNA is usually transcribed into DNA beforehand by techniques known in the art.

The present invention further relates to methods for the absolute quantification of nucleic acid sequences. Absolute quantification of a nucleic acid sequence or sequences according to the present invention refers to obtaining an absolute measure of the amount of the nucleic acid sequence or sequences in a sample present before the PCR reaction begins and/or subsequent analysis thereof. Subsequent analysis can include, among other things, determining, e.g., copy number of the target nucleic acid sequences.

EXAMPLES

Example 1

In order to examine the reliability of the method of the invention DNA samples with known concentrations were analyzed and the results were compared to the DNA concentrations used.

DNA samples of *Staphylococcus aureus* containing the target nucleic acid sequence from the 5' part of the 442 Sau3A1 genomic fragment, 256 basepairs, in pCR2.1-TOPO, cloned from *S. aureus* ATCC-25923, in a volume of 25 µl and concentrations of $10^6$, $10^5$, $10^4$, $10^3$, $10^2$, $10^1$ copies per 25 µl obtained by dilution were amplified in separate vials by 40 cycles of PCR on an ABI 7099HT version 2.3 real-time PCR cycler. For the PCR reaction Taqman Universal PCR mastermix of ABI and Taqman probes FAM-Black Hole Quencher 1 were used. Amplification curves were recorded.

Model function IF(n) was defined as follows, the parameters related to physical quantities that have an impact on the signals recorded were chosen as the absolute initial quantity of the target nucleic acid sequence $N_0$, and the parameters $E_0$, $\alpha$, $\epsilon$ and $\gamma$:

$$IF[n] = \frac{N_{uq}[n]I_{uq} + N_q[n]I_q}{1 + \gamma \cdot n},$$

wherein $$N_q[n] = N_p - N_{uq}[n],$$

and wherein $$N_{uq}[n] = N[n] + N_{suq}[n],$$

and wherein $$N_{suq}[n] = N_{suq}[n-1] + \beta \cdot N_q[n-1],$$

and wherein $$N[n] = N[n-1](1 + E[n]),$$

and wherein $$E[n] = E_0 - \alpha \left( \frac{N[n-1]}{N_p - N[n-1]} \right)^\epsilon,$$

wherein:
n=cycle number;
N(n)=number of target nucleic acid molecules at cycle n;
$N_0$=N(0) absolute initial number of target nucleic acid sequences;
$N_{uq}$(n)=number of unquenched fluorescent reporters at cycle n;

$I_{uq}$=fluorescent intensity parameter for unquenched fluorescent reporters;

$N_q(n)$=number of quenched fluorescent reporters at cycle n;

$I_q$=fluorescent intensity parameter for quenched fluorescent reporters;

γ=parameter related to the absorption properties of the container used for performing the amplification process;

$N_p$=initial number of fluorescent reporter probes;

$N_{suq}(n)$=number of spontaneously unquenched fluorescent reporters at cycle n;

β=fraction of fluorescent reporters that unquench spontaneously;

E(n)=amplification efficiency of cycle n;

$E_0$=initial amplification efficiency;

α=scaling factor related to the inhibition of the amplification process;

ε=parameter related to the sensitivity of the amplification process to PCR primer depletion.

In order to determine the best fit of the model to the amplification curve, the following operations were performed:

at first the parameter space was defined for each of the parameters $N_0$, α, $E_0$, ε, γ and divided into steps, i.e., $N_0$: from $10^0$ to $10^{10}$ with stepsize of $10^{0.5}$, α: from 1 to 2 with stepsize of 0.1, $E_0$: from 0 to 1 with stepsize of 0.1, ε: from 0.1 to 0.5 with stepsize of 0.05, γ was defined as 0.

Furthermore, values for $I_q$, $I_{uq}$ and β were estimated as follows: linear regression was performed for cycles 5 to 10 of the amplification curve and the intercept of the resulting fitted line divided by the number of quenched fluorophores Np was used as an estimate for Iq. $N_p$ was calculated as Np=$N_{Avogadro}$*$c_{reporter\ probe}$*V. $I_{uq}$ was estimated as $I_{uq}$=$I_q$/$(1-\eta_{QE})$ with $\eta_{QE}$=0.8. β was estimated as the slope of the linear regression of cycles 5 to 10 of the amplification curve.

The maximum cycle number $n_{max}$, defined as the upper limit of the fitting interval, was defined as the last cycle where the amplification curve was below 90% of its maximal value.

Subsequently start-values were defined for a number of parameters. Cycle number n was set to n=0. Parameters $N_0$, α, $E_0$, ε, γ were assigned values from their corresponding parameter space. $N_p$ was defined as the initial number of fluorescent reporter probes used for the amplification process, with Np=$N_{Avogadro}$*$C_{reporter\ probe}$*V. $I_q$, $I_{uq}$ and β were defined according to the estimate performed before. $N_{suq}(0)$ was set to $N_{suq}(0)$=0. $N_{uq}(0)$ was set to $N_{uq}(0)$=0. $N_q(0)$ was set to $N_q(0)$=$N_p$−$N_{uq}(0)$. $I_0$ was set to $$I[0] = \frac{N_{uq}[0]I_{uq} + N_q[0]I_q}{1+\gamma}.$$

Subsequently the cycle number was set to n=1 and the following iterative process was performed:

Determine efficiency E(n):

$$E[n] = E_0 - \alpha\left(\frac{N[n-1]}{N_p - N[n-1]}\right)^\varepsilon,$$

Determine number of target nucleic acid sequences N(n):

$$N[n]=N[n-1](1+E[n]),$$

Determine number of spontaneously unquenched fluorescent reporters $N_{suq}(n)$:

$$N_{suq}[n]=N_{suq}[n-1]+\beta \cdot N_q[n-1],$$

Determine number of unquenched fluorescent reporters $N_{uq}(n)$:

$$N_{uq}[n]=N[n]+N_{suq}[n],$$

Determine number of quenched fluorescent reporters $N_q(n)$:

$$N_q[n]=N_p-N_{uq}[n],$$

Determine fluorescent intensity I(n):

$$I[n] = \frac{N_{uq}[n]I_{uq} + N_q[n]I_q}{1+\gamma \cdot n}.$$

Evaluate n>$n_{max}$; YES=>calculate fitting error and proceed with the next set of parameter values for $N_0$, α, $E_0$, ε, γ; NO=>set n=n+1.

Evaluate $N_p$>N(n−1); YES=>proceed with step (a); NO=>set E(n)=0 and proceed with step (b).

The fitting error fit_err was calculated as a measure of the difference between the fit-function IF(n) and the amplification curve as $$\text{fit\_err}(N_0\_k1, \alpha\_k2, E_0\_k3, \varepsilon\_k4, \gamma\_k5) = \sum_{n=1}^{n_{max}}\left\{\frac{IF[n] - AC[n]}{AC[n]}\right\},$$

wherein AC(n) is the signal intensity value of the amplification curve at cycle n.

This process was repeated with different sets of values for parameters $N_0$, α, $E_0$, ε, γ until all combinations of parameter values defined during the initiation phase had been calculated.

The function IF(n) that yielded the minimal fitting error for a specific amplification curve was then selected as the best fit and the corresponding parameter values $N_0^\#$, $\alpha^\#$, $E_0^\#$, $\varepsilon^\#$, $\gamma^\#$ were identified.

Figure 3:
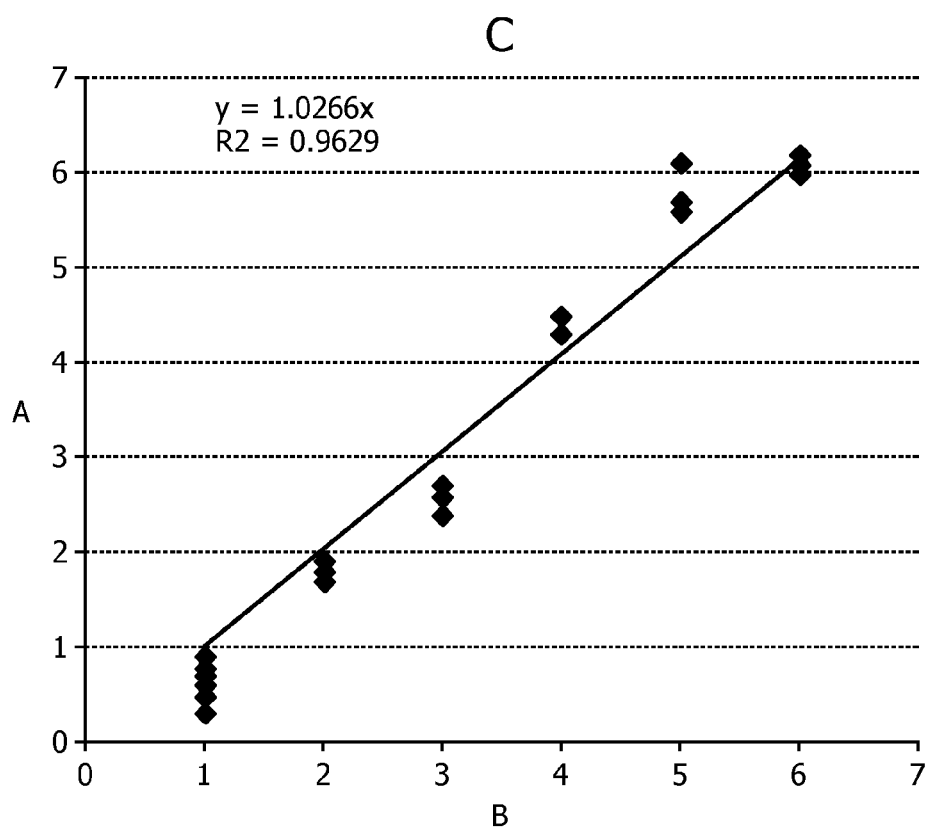
FIG. 3 shows the absolute initial amounts of target DNA in a series of samples (B) plotted against the results determined according to the present invention (A). The results of the analysis correspond with the initial amounts of target DNA that were present originally.

FIG. 3 shows the results of the analysis (A) in comparison with the actual amounts of target DNA that were used (B). The data points converge on a linear graph of Y=1.027x with a Pearson's coefficient of $R^2$=0.9629, indicating that the results of the analysis are in close correspondence to the DNA amounts that were originally used in the PCR reaction.

Example 2

Some parameters obtained by the method of the present invention can be used to evaluate the quality of the amplification process. In the following example, a plot of the parameters $E_0$ vs. α, obtained by a method of the present invention identified samples with poor amplification quality, suggesting that the data, e.g., the initial target nucleic acid sequence concentration, obtained for these samples may not be comparable to that of the other samples in the group. Furthermore, these parameters can be used to distinguish between reliable amplification curves and curves where no amplification reaction took place.

Thirty-six PCR reactions were performed on a Bio-Rad CFX real-time PCR instrument with software v1.1. using a TaqMan Universal master mix (2×): Applied Biosystems (4304437) lot K15898 (Jan. 31, 2010) and S. aureus PCR primers and probes: 1033-001 Sa__442_PR1129F23 10 μM, 1034-001 S.aur__442_R2 10 μM and 1035-001 S.aur__442_TQM2_FAM 10 μM. Samples were prepared as follows: Topo1/S. Aureus plasmid DNA was diluted so that samples of 0, $10^2$, $10^4$, and $10^6$ copies were obtained (13 samples with $10^6$ copies, 11 samples with $10^4$ copies, 8 samples with $10^2$ copies and 4 samples without target DNA (NTC)).

Model function IF(n) and parameters were defined as in Example 1. Parameter space was defined for each of the parameters, i.e., $N_0$: from $10^0$ to $10^{10}$ with stepsize of $10^{0.5}$, $\alpha$: from 1 to 3 with stepsize of 0.2, $E_0$: from 0 to 1 with stepsize of 0.01, $\epsilon$: from 0.1 to 0.7 with stepsize of 0.05, $\gamma$ was defined as 0. The remainder of the method was performed as described in Example 1.

Figure 4:
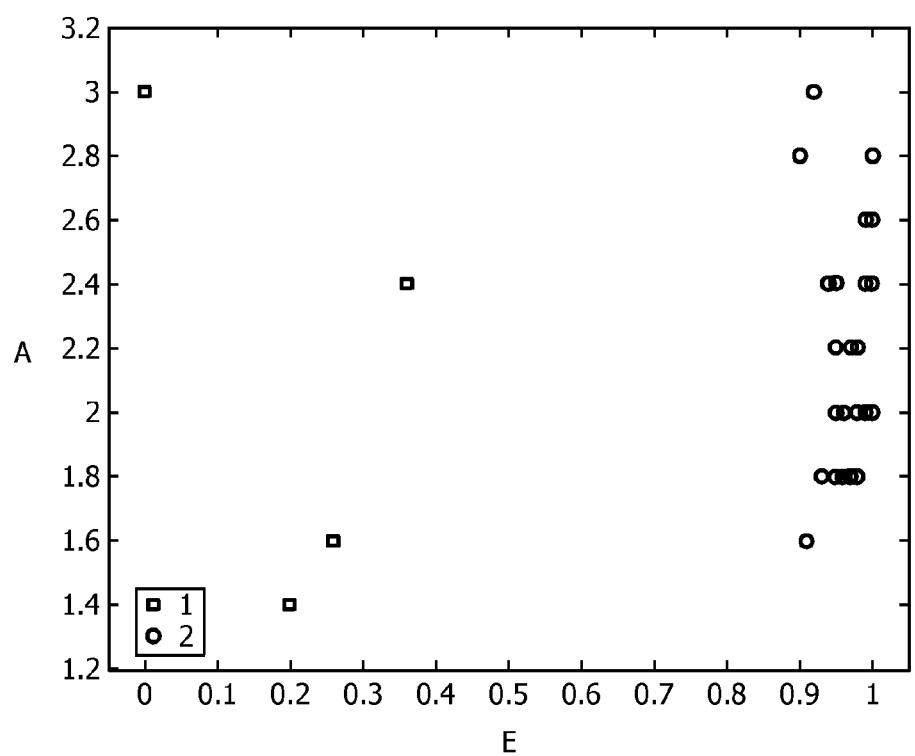
FIG. 4 shows parameters $E_0$ (E) and $\alpha$ (A), determined according to the present invention for a series of samples, plotted against each other. Circles denote regular samples containing target DNA while squares denote samples containing no target DNA. The presence of a distinct cluster comprising the data points for the regular samples indicates that $E_0$ and $\alpha$ can be used to identify and possibly exclude samples with dysfunctional amplification reactions, which otherwise might lead to misinterpretations.

FIG. 4 shows the resulting values of $\alpha$ (A) plotted against the values of $E_0$ (E) that were obtained. Most of the data points cluster on the right side of the graph, i.e., display high values for $E_0$. A few of the data points, however are located further on the left side, i.e., at lower levels of $E_0$. Interestingly, all of these data points correspond to samples that contained no target DNA at all. This suggest that $E_0$ and $\alpha$ may be used to identify data points that should be subjected to further examination in order to decide if they are the result of measurement artifacts.

Example 3

Some parameters obtained by the method of the present invention can be used to evaluate the quality of the amplification process. In the following example, a plot of parameters $E_0$ vs. $\epsilon$ obtained by a method of the present invention identified amplification reactions that had poor amplification quality, suggesting that the data, e.g., the initial nucleic acid sequence target concentration, obtained for these samples may not be comparable to that of the other samples.

DNA samples of *Staphylococcus aureus* where the target nucleic acid sequence was from the 5' part of the 442 Sau3A1 genomic fragment, 256 basepairs, in pCR2.1-TOPO, cloned from *S. aureus* ATCC-25923 in a volume of 25 μl and concentrations of $10^6$, $10^5$, $10^4$, $10^3$, $10^2$, $10^1$ copies per 25 μl obtained by dilution were amplified in separate vials by 40 cycles of PCR on an ABI 7099HT version 2.3 real-time PCR cycler. For the PCR reaction Taqman Universal PCR mastermix of ABI and Taqman probes FAM-Black Hole Quencher 1 were used. Amplification curves were recorded.

The remainder of the experiment was performed as described in Example 1.

Figure 5:
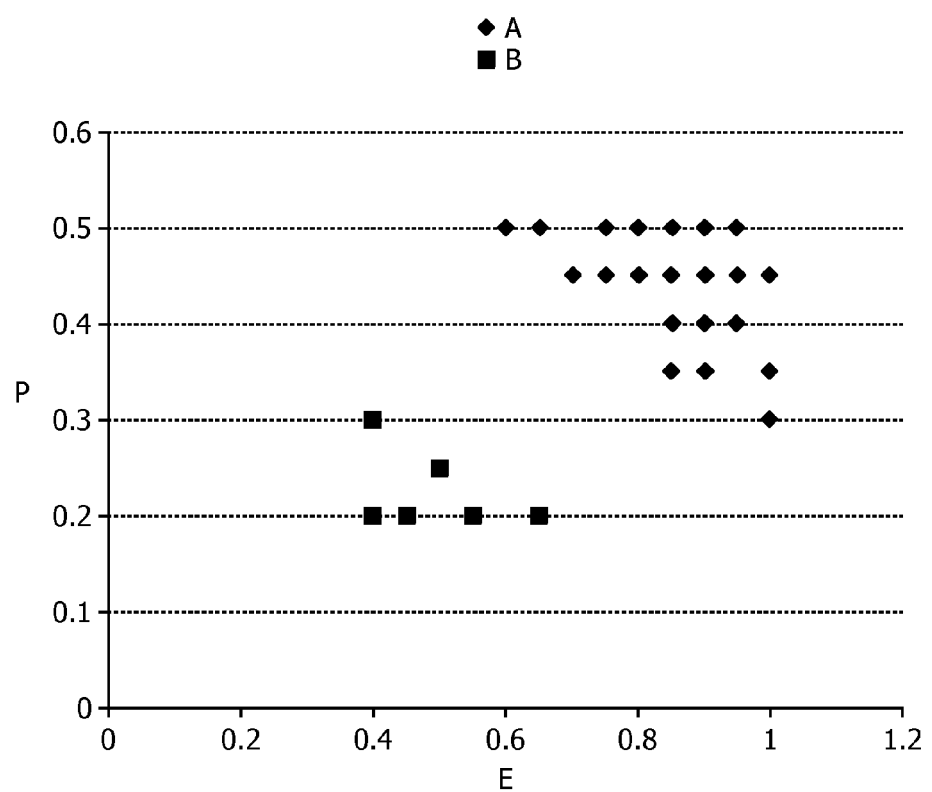
FIG. 5 shows parameters $E_0$ and $\epsilon$, determined according to the present invention for a series of samples, plotted against each other. Diamonds denote regular samples containing target DNA while squares denote samples containing no target DNA. The presence of distinct clusters comprising the data points for each of the sample types indicates that $E_0$ and $\epsilon$ can be used to identify and possibly exclude samples with dysfunctional amplification reactions, which otherwise might lead to misinterpretations.

FIG. 5 shows the resulting values of $\epsilon$ plotted against the values of $E_0$ that were obtained. Most of the data points cluster in the upper right corner of the graph. A few of the data points however are located on the lower left side of the graph. Interestingly, all of these data points correspond to samples that contained no target DNA at all. This suggests that $E_0$ and $\epsilon$ may be used to identify data points that should be subjected to further examination in order to decide if they are the result of measurement artifacts.

Example 4

PCR reactions were performed with two PCR samples—one with 49% faeces added, the other without faeces added—and amplification curves were obtained as described in the previous examples. Subsequently, the best fits of model functions IF(n) as well as the corresponding fit-parameters were obtained as described in the previous examples.

Figure 6A:
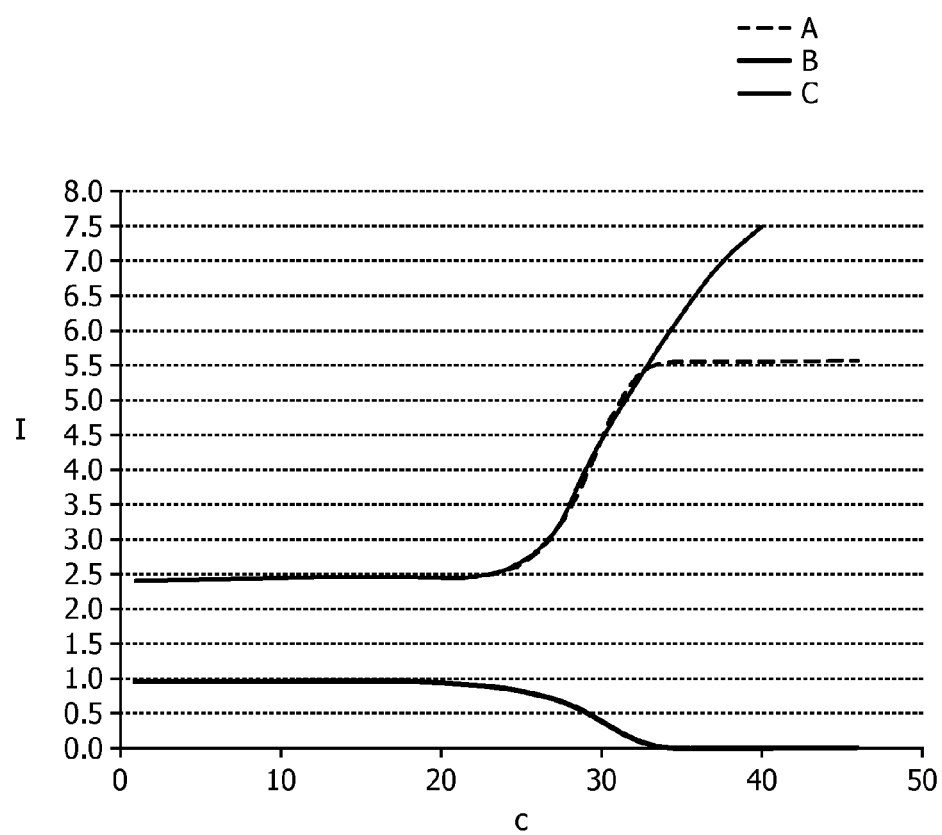
FIGS. 6A and 6B show plots of the amplification curves obtained (C), the best fits of model functions (A) as well as amplification efficiencies (B) over the course of the cycles of PCR reactions performed with two PCR samples—one with 49% feces added and the other without feces added. As described in example 4, a comparison of the plots of the amplification efficiency determined for the sample without feces (FIG. 6A) and the sample with feces (FIG. 6B) shows that the presence of feces has a significant and detrimental impact on the efficiency of the amplification reaction: Amplification efficiency in FIG. 6A starts at 1.0, while amplification efficiency in FIG. 6B starts at 0.51.
Figure 6B:
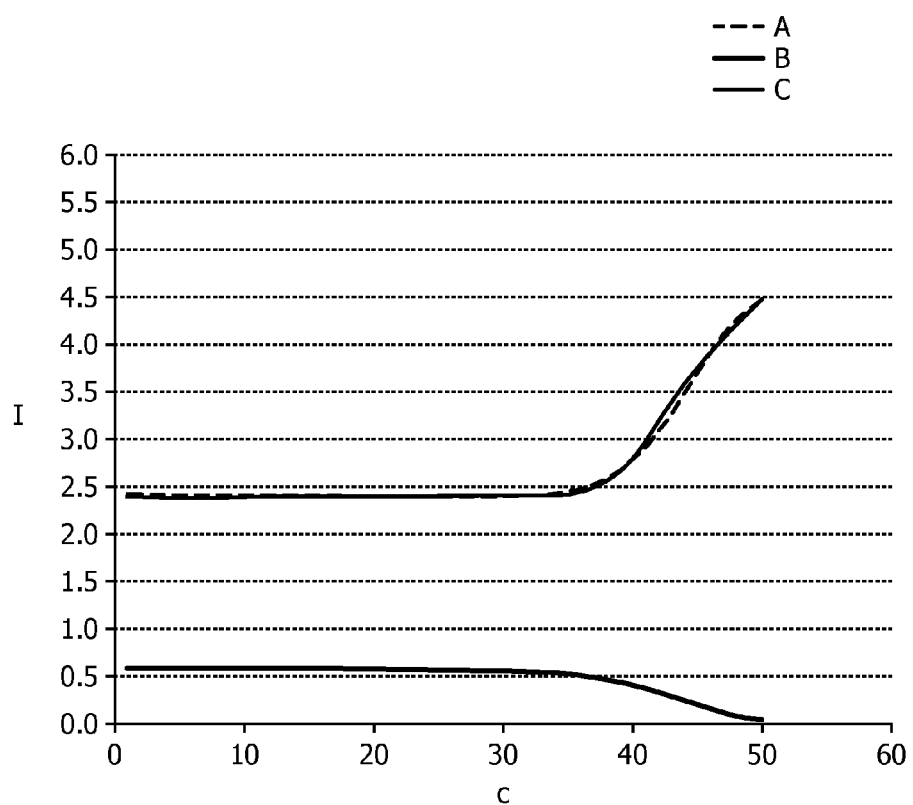

FIGS. 6A and 6B show plots of the amplification curves obtained (C), the best fits of the model functions (A) as well as the amplification efficiencies (B) over the course of the cycles of each of the amplification reactions. A comparison of the plots of the amplification efficiency determined for the sample without faeces (FIG. 6A) and the sample with faeces (FIG. 6B) showed that the presence of faeces had a significant and detrimental impact on the efficiency of the amplification reaction. Amplification efficiency in FIG. 6A starts at 1.0, while amplification efficiency in FIG. 6B starts at 0.51. The plot of the amplification efficiency as determined by the methods of the present invention is thus, a useful tool to reveal such significant and detrimental effects.

The invention claimed is:

1. A computer implemented method for obtaining information for automatic quantification of nucleic acid sequences from an amplification curve of a target nucleic acid sequence obtained from an amplification reaction process, comprising the steps:
   (a) defining, using a computer, at least one model function that describes the amplification curve and that contains at least one parameter that is related to a physical quantity that has an impact on the signals that are recorded,
   (b) fitting, using the computer, said model function to the amplification curve,
   (c) obtaining, using the computer, information with respect to said physical quantity by identifying the value of said at least one parameter that results in a best fit of the model function wherein the at least one parameter is at least one of an absolute initial quantity of the target nucleic acid sequence N0, and parameters E0, $\alpha$, $\epsilon$ and $\gamma$, and wherein the model function is defined as IF(n), $$IF[n] = \frac{N_{uq}[n]I_{uq} + N_q[n]I_q}{1 + \gamma \cdot n},$$

wherein $$N_q[n] = N_p - N_{uq}[n],$$

and wherein $$N_{uq}[n] = N[n] + N_{suq}[n],$$

and wherein $$N_{suq}[n] = N_{suq}[n-1] + \beta \cdot N_q[n-1],$$

and wherein $$N[n] = N[n-1](1+E[n]),$$

and wherein $$E[n] = E_0 - \alpha \left( \frac{N[n-1]}{N_p - N[n-1]} \right)^\epsilon$$

wherein
n=cycle number;
N(n)=number of target nucleic acid molecules at cycle n;
$N_0$=N(0) absolute initial number of target nucleic acid sequence;
$N_{uq}(n)$=number of unquenched fluorescent reporters at cycle n;
$I_{uq}$=fluorescence intensity parameter for unquenched fluorescent reporters;
$N_q(n)$=number of quenched fluorescent reporters at cycle n;
$I_q$=fluorescent intensity parameter for quenched fluorescent reporters;
$\gamma$=parameter related to the absorption properties of the container used for performing the amplification process;
$N_p$=initial number of fluorescent reporter probes;

$N_{suq}(n)$=number of spontaneously unquenched fluorescent reporters at cycle n;
$\beta$=fraction of fluorescent reporters that unquench spontaneously;
E(n)=amplification efficiency of cycle n;
$E_0$=initial amplification efficiency;
$\alpha$=scaling factor related to inhibition of the amplification process;
$\epsilon$=parameter related to the sensitivity of the amplification process to PCR primer depletion.

2. The method according to claim 1, wherein the physical quantity is a physical quantity selected from the following: a physical quantity related to generation of signal-noise during the amplification reaction process, a physical quantity related to inhibition of the amplification reaction process, a physical quantity related to spontaneous unquenching of fluorophores during the amplification reaction process.

3. The method according to claim 1, wherein the physical quantity is selected from the following:
an absolute initial quantity of the target nucleic acid sequence,
initial amplification efficiency of the target nucleic acid sequence,
a degree of inhibition of the amplification reaction,
a degree of signal absorption by a reaction container used for the amplification reaction process.

4. The method according to claim 1 further comprising step (d), wherein the information that is obtained is the fluorescence threshold-level ("Ct-value") for the amplification curve, with
(d) using the best fit of said model function to determine a Ct-value for said amplification curve.

5. The method according to claim 1, wherein one target nucleic acid sequence in a sample is analyzed at a same time.

6. The method according to claim 1, wherein more than one target nucleic acid sequence in a sample is analyzed at a same time.

7. The method according to claim 1, wherein a representation of the signals recorded over a course of cycles of an amplification reaction, after a reduction of disturbances resulting from optical crosstalk and auto fluorescence, is used as the amplification curve.

8. The method according to claim 1, wherein all steps are performed in a completely automated fashion, i.e., without any human interaction during polymerase chain reaction process.

9. A non-transitory machine readable medium having stored thereon instructions for obtaining, using a computer, information from an amplification curve of a target nucleic acid sequence obtained from an amplification reaction process, the medium comprising instructions for
(a) defining at least one model function that describes the amplification curve and that contains at least one parameter that is related to a physical quantity that has an impact on signals that are recorded,
(b) fitting said model function to the amplification curve,
(c) obtaining information with respect to said physical quantity by identifying the value of said at least one parameter that results in a best fit of the model function
wherein the at least one parameter is at least one of an absolute initial quantity of the target nucleic acid sequence N0, and parameters E0, $\alpha$, $\epsilon$ and $\gamma$,
and wherein the model function is defined as IF(n), wherein $$IF[n] = \frac{N_{uq}[n]I_{uq} + N_q[n]I_q}{1 + \gamma \cdot n},$$

and wherein $$N_q[n] = N_p - N_{uq}[n],$$

and wherein $$N_{uq}[n] = N[n] + N_{suq}[n],$$

and wherein $$N_{suq}[n] = N_{suq}[n-1] + \beta \cdot N_q[n-1],$$

and wherein $$N[n] = N[n-1](1 + E[n]),$$

and wherein $$E[n] = E_0 - \alpha \left( \frac{N[n-1]}{N_p - N[n-1]} \right)^\epsilon$$

wherein
n=cycle number;
N(n)=number of target nucleic acid molecules at cycle n;
$N_0$=N(0) absolute initial number of target nucleic acid sequence;
$N_{uq}(n)$=number of unquenched fluorescent reporters at cycle n;
$I_{uq}$=fluorescence intensity parameter for unquenched fluorescent reporters;
$N_q(n)$=number of quenched fluorescent reporters at cycle n;
$I_q$=fluorescent intensity parameter for quenched fluorescent reporters;
$\gamma$=parameter related to the absorption properties of the container used for performing the amplification process;
$N_p$=initial number of fluorescent reporter probes;
$N_{suq}(n)$=number of spontaneously unquenched fluorescent reporters at cycle n;
$\beta$=fraction of fluorescent reporters that unquench spontaneously;
E(n)=amplification efficiency of cycle n;
$E_0$=initial amplification efficiency;
$\alpha$=scaling factor related to inhibition of the amplification process;
$\epsilon$=parameter related to the sensitivity of the amplification process to PCR primer depletion.

10. An apparatus for the analysis of nucleic acid samples comprising:
one or more processors;
a memory storing a program of instructions for
obtaining information from an amplification curve of a target nucleic acid sequence obtained from an amplification reaction process, comprising the steps:
(a) defining at least one model function that describes the amplification curve and that contains at least one parameter that is related to a physical quantity that has an impact on the signals that are recorded,
(b) fitting said model function to the amplification curve, (c) obtaining information with respect to said physical quantity by identifying the value of said at least one parameter that results in a best fit of the model function wherein the at least one parameter is at least one of an absolute initial quantity of the target nucleic acid sequence N0, and parameters E0, $\alpha$, $\epsilon$ and $\gamma$, and wherein the model function is defined as IF(n), wherein $$IF[n] = \frac{N_{uq}[n]I_{uq} + N_q[n]I_q}{1 + \gamma \cdot n},$$

$$N_q[n] = N_p - N_{uq}[n],$$

and wherein $$N_{uq}[n] = N[n] + N_{suq}[n],$$

and wherein $$N_{suq}[n] = N_{suq}[n-1] + \beta \cdot N_q[n-1],$$

and wherein $$N[n] = N[n-1](1 + E[n]),$$

$$E[n] = E_0 - \alpha \left( \frac{N[n-1]}{N_p - N[n-1]} \right)^\varepsilon$$

and wherein
wherein
- n=cycle number;
- N(n)=number of target nucleic acid molecules at cycle n;
- $N_0$=N(0) absolute initial number of target nucleic acid sequence;
- $N_{uq}$(n)=number of unquenched fluorescent reporters at cycle n;
- $I_{uq}$=fluorescence intensity parameter for unquenched fluorescent reporters;
- $N_q$(n)=number of quenched fluorescent reporters at cycle n;
- $I_q$=fluorescent intensity parameter for quenched fluorescent reporters;
- $\gamma$=parameter related to the absorption properties of the container used for performing the amplification process;
- $N_p$=initial number of fluorescent reporter probes;
- $N_{suq}$(n)=number of spontaneously unquenched fluorescent reporters at cycle n;
- $\beta$=fraction of fluorescent reporters that unquench spontaneously;
- E(n)=amplification efficiency of cycle n;
- $E_0$=initial amplification efficiency;
- $\alpha$=scaling factor related to inhibition of the amplification process;
- $\epsilon$=parameter related to the sensitivity of the amplification process to PCR primer depletion.

* * * * *